US007396350B2

(12) United States Patent
Mishima et al.

(10) Patent No.: US 7,396,350 B2
(45) Date of Patent: Jul. 8, 2008

(54) DISPOSABLE DIAPER

(75) Inventors: Yoshitaka Mishima, Kagawa-ken (JP); Yuko Matsuda, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/626,472

(22) Filed: Jan. 24, 2007

(65) Prior Publication Data

US 2007/0219522 A1 Sep. 20, 2007

(30) Foreign Application Priority Data

Mar. 16, 2006 (JP) ............................. 2006-072959

(51) Int. Cl.
*A61F 13/15* (2006.01)
(52) U.S. Cl. ............................ 604/385.28; 604/385.27; 604/385.24; 604/385.101; 604/385.26
(58) Field of Classification Search ............ 604/385.01, 604/385.101, 385.16, 385.21, 385.22, 385.24, 604/385.26, 385.27, 385.28, 385.25
See application file for complete search history.

(56) References Cited

U.S. PATENT DOCUMENTS

| 4,695,278 | A | 9/1987 | Lawson |
| 4,895,568 | A | 1/1990 | Enloe |
| 5,108,820 | A | 4/1992 | Kaneko et al. |
| 5,167,653 | A | 12/1992 | Igaue et al. |
| 5,295,986 | A | 3/1994 | Zehner et al. |
| 5,334,176 | A | 8/1994 | Buenger et al. |
| 5,460,622 | A | 10/1995 | Dragoo et al. |
| 5,575,785 | A | 11/1996 | Gryskiewicz et al. |
| 5,620,431 | A | 4/1997 | LeMahieu et al. |
| 6,022,338 | A | 2/2000 | Putzer |
| 6,156,024 | A | 12/2000 | Schulte et al. |
| 6,222,092 | B1 | 4/2001 | Hansen et al. |
| 6,413,248 | B1 | 7/2002 | Mizutani |
| 6,482,195 | B1 | 11/2002 | Kumasaka |
| 6,706,029 | B1 | 3/2004 | Suzuki et al. |
| 6,890,327 | B2 | 5/2005 | Suzuki et al. |
| 2005/0182381 | A1 | 8/2005 | Suzuki et al. |
| 2005/0273073 | A1* | 12/2005 | Suzuki et al. ......... 604/385.101 |

FOREIGN PATENT DOCUMENTS

| EP | 0 978 265 A2 | 2/2000 |
| JP | 2174845 A | 7/1990 |
| JP | 3218752 A | 9/1991 |
| JP | 467864 A | 3/1992 |
| JP | 8-322878 A | 12/1996 |
| JP | 928732 A | 2/1997 |
| JP | 9-28732 A | 4/1997 |
| JP | 10-57409 A | 3/1998 |
| JP | 10-192338 A | 7/1998 |
| JP | 200245396 A | 2/2002 |
| JP | 2002-315776 A | 10/2002 |
| JP | 2002-345887 A | 12/2002 |
| JP | 2004-248769 A | 9/2004 |
| JP | 2005-342203 | 12/2005 |

\* cited by examiner

*Primary Examiner*—Jacqueline F. Stephens
(74) *Attorney, Agent, or Firm*—Lowe Hauptman Ham & Berner LLP

(57) ABSTRACT

A diaper is provided on its inner side with a tufted sheet strip assembly. The assembly includes a plurality of sheet strips, a sheet-like base member to which fixed end zones of the respective sheet strips are permanently bonded, and elastically biasing element adapted to space a transversely intermediate zone of the sheet-like base member from the inner side of the diaper.

9 Claims, 9 Drawing Sheets

DISPOSABLE DIAPER

BACKGROUND OF THE INVENTION

The present invention relates generally to a disposable diaper.

Conventionally it has been well known to provide disposable diapers with means adapted to prevent loose passage discharged by the wearer from flowing along the wearer's skin toward the external genital and/or to prevent urine discharged by the wearer from flowing toward the wearer's anus. In the known diaper, for example, in Japanese Unexamined Patent Application Publication No. 2005-342203 (REFERENCE), any one of the crotch region, the front waist region and the rear waist region of the disposable diaper is formed on the inner side thereof with a plurality of nonwoven fabric sheet strips assembled together so as to be tufted. In the case of such assembly formed in the crotch region, the assembly extends across the block of body fluid absorbent material so as to bisect the crotch region into front and rear halves. With this diaper put on the wearer's body, plurality of the sheet strips come in contact with the wearer's skin and thereby prevent loose passage from flowing toward the external genital and/or prevent urine from flowing toward the anus.

In the diaper disclosed in REFERENCE, each of the nonwoven fabric sheet strips has one end zone fixed to the liquid-pervious inner sheet used to cover the block of body fluid absorbent material. With such a construction, the assembly of the sheet strips is apt to be spaced from the skin as the diaper put on the wearer's body slips down and eventually the crotch region is spaced from the skin. Consequentially, it will be difficult to prevent loose passage and/or urine from flowing along the skin.

SUMMARY OF THE INVENTION

It is an object of the present invention to improve the disposable diaper formed on the inner side thereof with the sheet strip assembly to ensure that the sheet strip assembly is not easily spaced from the wearer's skin even if the diaper slips down and the inner surface of the diaper is spaced from the wearer's skin.

According to the present invention, there is provided a disposable diaper comprising a crotch region having a back-and-forth direction and a transverse direction orthogonal to the back-and-forth direction, a front waist region extending forward from the crotch region and a rear waist region extending rearward from the crotch region, these regions respectively having inner surfaces and outer surfaces opposed to the inner surfaces wherein a tufted assembly comprising a plurality of sheet strips is attached to the inner surface in any one of the regions so as to extend in the transverse direction in orthogonal relationship with a center line extending in the back-and-forth direction so as to bisect widths of the respective regions, The diaper further comprises: the assembly comprising a plurality of sheet strips, a sheet-like base member extending in the transverse direction and supporting thereon the sheet strips each having at least one end zone thereof permanently bonded to the sheet-like base member, and elastically biasing means adapted to space at least a transversely middle zone of the sheet-like base member from the inner surface in a direction defined from the outer side toward the inner surface.

According to one preferred embodiment of the present invention, at least a part of the sheet-like base member constituting the assembly is elastically stretchable/contractible in the transverse direction and, in stretched state, end zones of the sheet-like base member opposed to each other in the transverse direction are bonded to the inner surface so as to ensure that the sheet-like base member serves as the elastically biasing means.

According to another preferred embodiment of the present invention, the inner surface of the diaper is provided with a pair of leak-barrier cuffs extending along side edges of the crotch region opposed to each other in the transverse direction and further into the front and rear waist region, each of the leak-barrier cuffs having a fixed edge bonded to the inner surface and a free edge extending in parallel to the fixed edge and cooperating with an elastic member stretched in the back-and-forth direction and bonded in such stretched state to the free edge, and the end zones of the sheet-like base member opposed to each other in the transverse direction are bonded to respective the free edges so as to ensure that the free edges serve as the elastically biasing means.

According to still another preferred embodiment of the present invention, the inner surface of the diaper is provided with an elasticized sheet including a first elastic member and a second elastic member extending so as to intersect with each other and to describe a X-shape in the crotch region, the first and second elastic members have lateral zones extending from the crotch region toward the front waist region and the rear waist region and a joint zone joining respective lateral zones to each other, the respective lateral zones being bonded to the inner surface while the joint zone is left free from the inner surface and includes the intersection of the first elastic member and the second elastic member, the elasticized sheet being elastically stretchable/contractible in directions in which the first elastic member and the second elastic member extend, the assembly lies further inside the elasticized sheet and being bonded to the joint zone so as to ensure that the elasticized sheet serves as the elastically biasing means.

In the disposable diaper according to the present invention, the sheet strip assembly in tufted state extends on the inner surface of the diaper in the transverse direction and is under the effect of the elastically biasing means adapted to space the transversely intermediate zone from the inner surface of the diaper. As an advantageous result, the assembly is spaced from the crotch region of the diaper so as to be kept in contact with the skin even if the crotch region of the diaper put on the wearer's body moves off from the skin.

The present invention may be exploited in the manner that at least a part of the sheet-like base member constituting the assembly is elastically stretchable/contractible in the transverse direction of the diaper and, in such stretched state, the transversely opposite end zones of the sheet-like base member are bonded to the inner surface of the diaper. According to this embodiment, the sheet-like base member serving as the elastically biasing means contracts so as to space the assembly from the inner surface of the diaper, allowing the individual sheet strips to come in contact with the skin as the diaper is put on the wearer's body and curves in the transverse direction so that the crotch region becomes convex outward.

The present invention may be also exploited in the manner that the diaper is provided on its inner surface with the leak-barrier cuffs and the transversely opposite end zones of the sheet-like base member constituting the assembly are bonded to the respective free edges of the leak-barrier cuffs maintained in stretched state. According to this embodiment, the free edges serve as the elastically biasing means adapted to space the assembly from the inner surface of the crotch region and thereby to bring the sheet strips in contact with the skin even if the crotch region of the diaper is spaced from the skin.

The present invention may be also exploited in the manner that the first elastic member and the second elastic member intersect with each other in stretched state in the crotch region of the diaper serve as the elastically biasing means. According to this embodiment, the first elastic member and the second elastic member contract as the diaper is put on the wearer's body and curves in the back-and-forth direction so that the crotch region becomes convex outwardly of the diaper. Contraction of the first elastic member and the second elastic member causes the assembly to be spaced from the inner surface of the crotch region and to come in contact with the skin.

DETAILED DESCRIPTION OF THE PREFERRED EMBODIMENTS

Details of a disposable diaper according to the present invention will be more fully understood from the description given hereunder with reference to the accompanying drawings.

Figure 1:
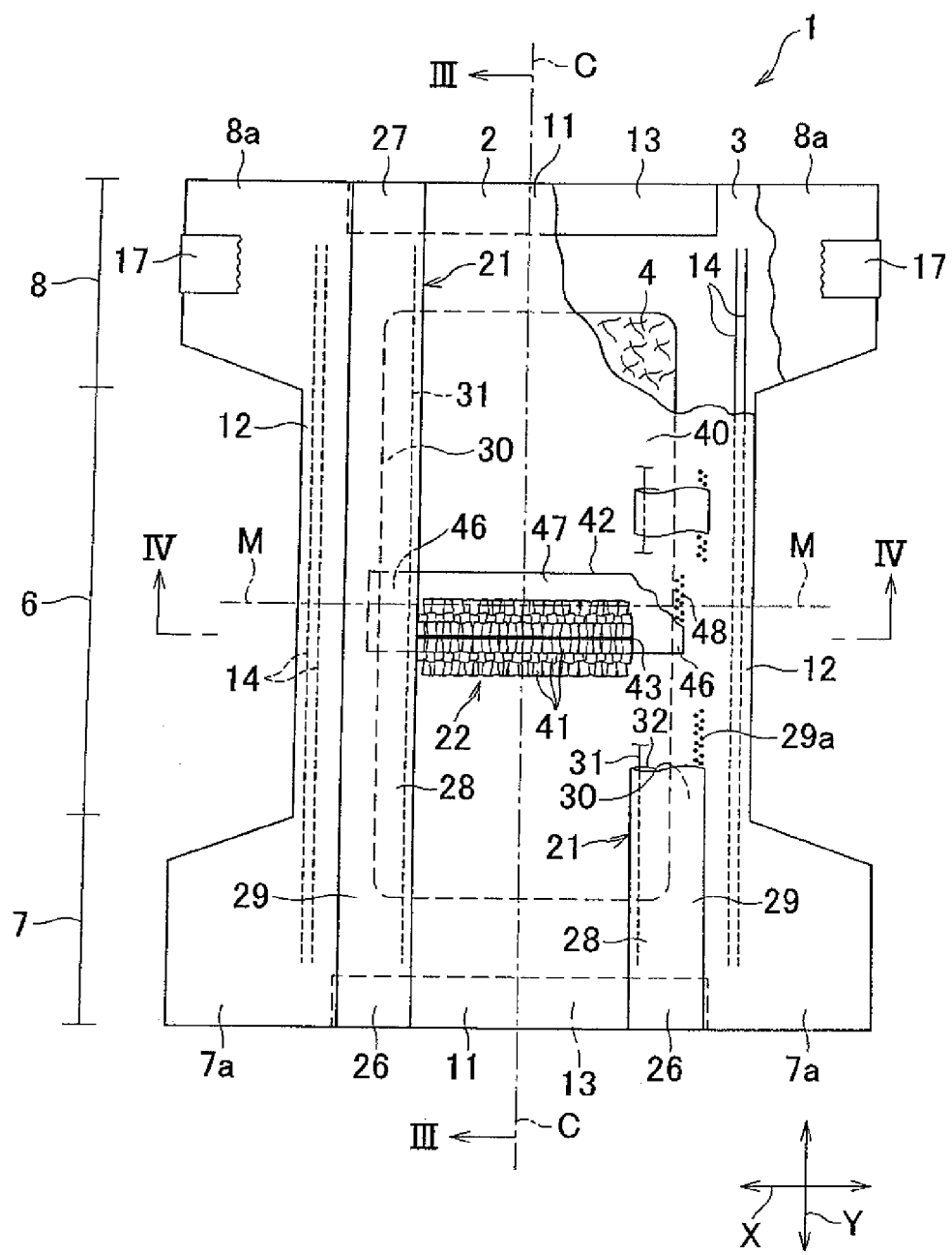
FIG. 1 is a partially cutaway plan view showing a diaper according to the present invention.

FIG. 1 is a partially cutaway plan view showing a disposable diaper 1. The diaper 1 comprises a liquid-pervious topsheet 2, a liquid-impervious backsheet 3 and a body fluid absorbent core 4 sandwiched between these two sheets 2, 3 wherein double-headed arrows X and Y indicate a transverse direction and a back-and-forth direction of the diaper 1 which are orthogonal to each other. The diaper 1 is configured so as to define, as viewed in the back-and-forth direction Y, a crotch region 6, a front waist region 7 extending forward from the crotch region 6 and a rear waist region 8 extending rearward from the crotch region 6 wherein the front and rear regions 7, 8 are respectively formed with a pair of wings 7a, 7a and a pair of wings 8a, 8a. Such diaper 1 has an hourglass-like planar shape contoured by a pair of ends 11 extending in the transverse direction X and a pair of side edges 12 extending in the back-and-forth direction Y. The side edges 12 bend or curve so as to be convex toward a longitudinal center line C-C bisecting a width of the diaper 1 in the crotch region 6. The core 4 extends over the crotch region 6 and further into the front and rear waist regions 7, 8. the core 4 is sandwiched between the topsheet 2 and the backsheet 3 both extending outward beyond a peripheral edge of the core 4 so as to be put flat together and bond to each other. Along the respective ends 11 of the front and rear waist regions 7, 8, waist-surrounding elastic members 13 are sandwiched between the topsheet 2 and the backsheet 3 so as to extend in the transverse direction X and bonded in a stretched state to at least one of these sheets 2, 3. Along the respective side edges 12 in the crotch region 6, a plurality of leg-surrounding elastic members 14 are sandwiched between the topsheet 2 and the backsheet 3 so as to extending in the back-and-forth direction Y and bonded in stretched state to at least one of the topsheet 2 and the backsheet 3. In the rear waist region 8, a pair of fastening tape strips 17 coated with a pressure-sensitive adhesive (not shown) are attached to the side edges 12, respectively, in a manner that these fastening tape strips 17 can be laterally folded. The topsheet 2 defines the inner side of the diaper 1 facing the wearer's skin while the backsheet 3 defines the outer side of the diaper 1 facing the diaper wearer's clothes. The inner side of the diaper 1 is provided with a pair of leak-barrier cuffs 21 extending in parallel in the back-and-forth direction and a sheet strip assembly 22 extending in the transverse direction X so as to serve as a barrier against an undesirable flow of body fluids. In such diaper 1, the topsheet 2, the core 4 and the backsheet 3 are placed one upon another to define a body fluid absorbent assembly 40.

Each of the leak-barrier cuffs 21 is formed by sheet material such as a water-repellent or liquid-impervious nonwoven fabric or a plastic film and comprises front and rear ends 26, 27 both extending in the transverse direction X, on one hand, and a free edge 28 and a fixed edge 29 both extending in the back-and-forth direction Y, on the other hand. The front end 26, the rear end 27 and the fixed edge 29 are bonded to the topsheet 2 by an adhesive 29a or welding technique. The free edge 28 is left free from the topsheet 2 and includes a sleeve 32 extending in the back-and-forth direction Y. An elastic member 31 is attached in stretched state to the inner side of the sleeve 32 so that the free edge 28 may be stretchable/contractible in the back-and-forth direction Y and cooperate with the topsheet to form a pocket 30 adapted to be opened toward the longitudinal center line C-C (See FIGS. 4 and 6).

The sheet strip assembly 22 extends across the body fluid absorbent assembly 40 between the pair of leak-barrier cuffs 21, 21 and comprises a plurality of individual sheet strips 41 made of a nonwoven fabric or a plastic film and a sheet-like base member 42 formed from a nonwoven fabric, a plastic film or the like.

Figure 2:
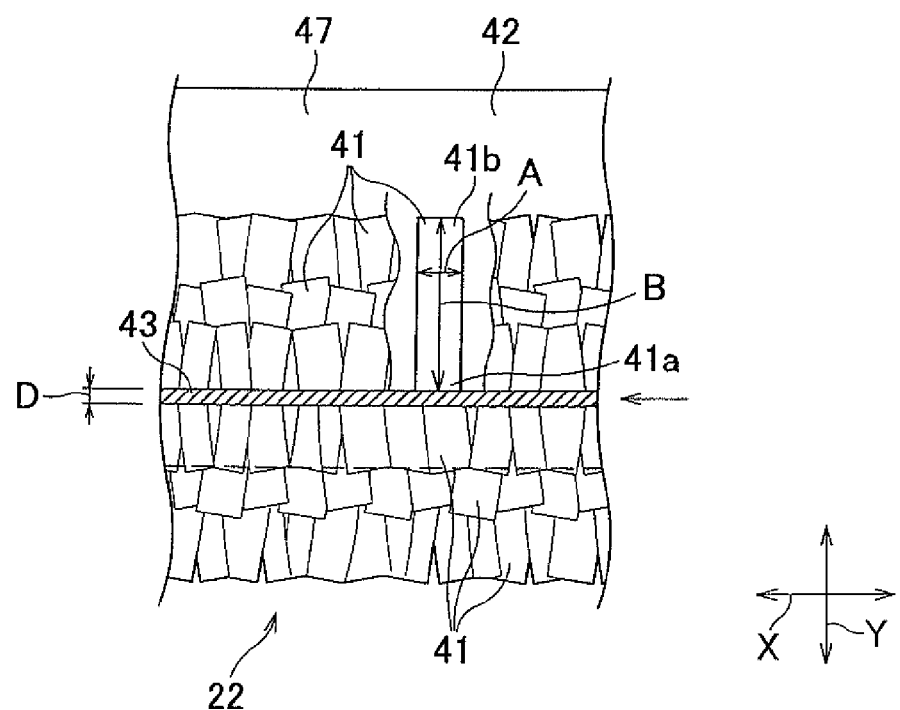
FIG. 2 is a scale-enlarged diagram illustrating a part of FIG. 1.
Figure 3:
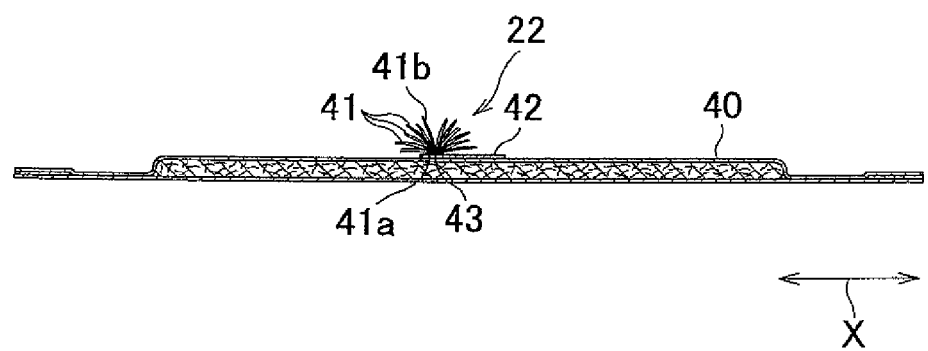
FIG. 3 is a sectional view taken along the line III-III in FIG. 1.

FIG. 2 is a scale-enlarged diagram illustrating a part of the sheet strip assembly 22. As illustrated, each of the individual sheet strips 41 has a fixed end 41a and a free end 41b wherein the fixed end 41a extends in the transverse direction X and is permanently bonded to the sheet-like base member 42 by a welding technique or an adhesive along a bonding line 43 having a dimension D in the back-and-forth direction Y while the free end 41b is deformable. The fixed end 41a of the individual sheet strip 41 may be directly fixed to the sheet-like base member 42 or fixed to the fixed end 41a of the adjacent sheet strip 41 which overlaps the former sheet strip 41 and then collectively bonded to the sheet-like base member 42. The sheet-like base member 42 is at least partially stretchable/contractible in the transverse direction X and the back-and-forth direction Y, at least in the transverse direction X. Outside the body fluid absorbent assembly 40, transversely opposite end zones 46 (See FIG. 1) of the sheet-like base member 42 are bonded in transversely stretched state to the topsheet 2 by a hot melt adhesive 48 or suitable welding technique. An intermediate zone 47 extending between the end zones 46 is left free from the topsheet 2 (See FIG. 1). While FIG. 3 shows a plurality of the individual sheet strip 41 including, in addition to those substantially collapsed onto the topsheet 2, those rising on the topsheet 2 at various angles with respect to the topsheet 2, these individual sheet strips 41 are arranged side-by-side each having a width A extending in the transverse direction X and a length B extending in the back-and-forth direction Y so far as viewed in FIG. 2. The individual sheet strip 41 preferably has the width A in a range of 2 to 15 mm and the length B in a range of 5 to 70 mm. The preferred bonding line 43 has the dimension D in a range of 1 to 5 mm and is selectively located in the back-and-forth direction Y so that the sheet strip assembly 22 may be formed between external genital and anus of the diaper wearer. The bonding line 43 exemplarily shown in FIG. 1 is located aside from a transverse middle line M-M bisecting the dimension of the diaper 1 toward the front waist region 7.

FIG. 3 is a sectional view taken along the line III-III in FIG. 1 corresponding to the longitudinal center line C-C. The individual sheet strips 41 successively overlap one another in a thickness direction thereof and have the respective fixed ends 41a welded together along the bonding line 43. From the fixed ends 41a toward the free ends 41b, the individual sheet strips 41 are gradually spaced from one another so as to obtain the tufted sheet strip assembly 22.

Figure 4:
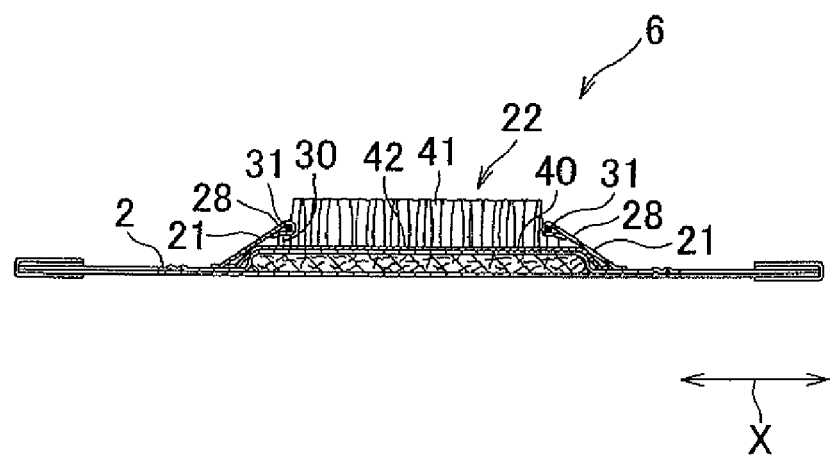
FIG. 4 is a sectional view taken along the line IV-IV in FIG. 1.

FIG. 4 is a sectional view taken along the line IV-IV in FIG. 1. The sheet strip assembly 22 is shown with the sheet-like base member 42 thereof being elastically stretched in the transverse direction X and placed upon the topsheet 2. The leak-barrier cuffs 21 respectively provided along the transversely opposite side edges of the crotch region 6 are shown with the elastic members 31 provided along the free edges 28 being stretched in the back-and-forth direction Y and the free edges 28 being substantially collapsed onto the sheet strip assembly 41.

Figure 5:
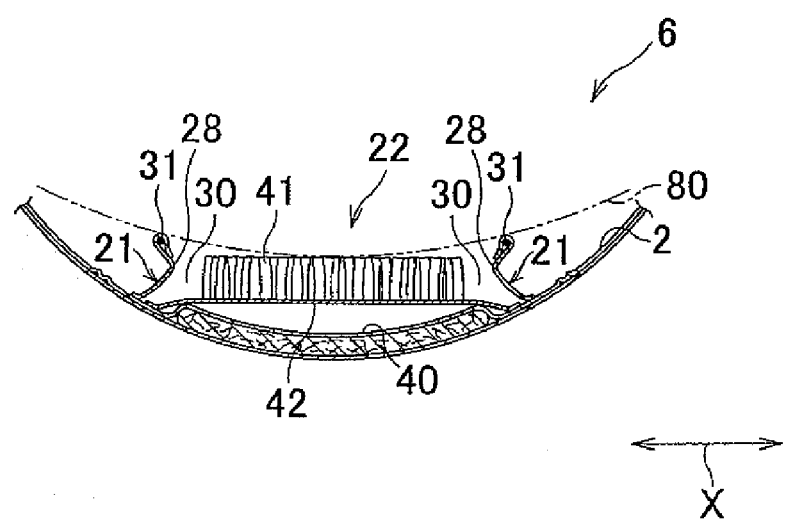
FIG. 5 is a view similar to FIG. 4, showing the diaper as put on the wearer's body.

FIG. 5 shows the crotch region 6 of FIG. 4, with the diaper 1 being put on the wearer's body. In the diaper 1 put on the wearer's body, the front and rear waist regions 7, 8 are connected to each other along the side edges thereof by means of the fastening tape strips 17 and the diaper 1 as a whole is curved in a U-shape in the back-and-forth direction Y with the topsheet 2 inside. Thereupon, contraction of the elastic members 31 for the leak-barrier cuffs 21 causes the free edges 28 of the respective leak-barrier cuffs 21 to be spaced from the topsheet 2 and the pockets 30 to be significantly opened. The crotch region 6 is curved in the transverse direction X between the wearer's thighs (not shown) as to be convex outward and the topsheet 2 is spaced from the wearer's crotch region skin, i.e., moved downward as viewed in FIG. 5. In the sheet strip assembly 22, however, the sheet-like base member 42 contracts from the state shown in FIG. 4 in the transverse direction X and thereby biases the sheet strip assembly 22 as a whole to be spaced from the topsheet and to come in contact with or to come close to the wearer's skin 80. The sheet strip assembly 22 in this state prevents urine discharged by the wearer from flowing along the skin toward the anus and/or loose passage discharged by the wearer from flowing along the skin toward the external genital. The sheet-like base member 42 of the sheet strip assembly 22 serves for fixation of the individual sheet strips 41 and simultaneously serves as elastically biasing means for the sheet strip assembly 22. Preferably, the sheet-like base member 42 is elastically contractible at least by 10% relative to its length in the transverse direction X stretched in this direction X as shown by FIG. 4. Elastically contractile force of the sheet-like base member 42 as well as resultant dimension thereof is preferably selected so as to eliminate a possibility that the width of the diaper 1 in the crotch region 6 might be unacceptably reduced.

In the diaper 1 as has been described above, a stock material for the topsheet 2 may be selected from the group including a nonwoven fabric and a plastic film which are liquid-pervious. A stock material for the backsheet 3 may be selected from the group including a plastic film, a nonwoven fabric and a laminate consisting of a plastic film and a nonwoven fabric. The absorbent core 4 may be formed from coveloop a body fluid absorbent material such as fluff pulp fibers or a mixture of fluff pulp fibers and super-absorbent polymer particles with a liquid-pervious and liquid-spreadable material such as a tissue paper or a nonwoven fabric. The leak-barrier cuffs 21 may be formed from a water-repellent or liquid-impervious sheet material such as a nonwoven fabric or a plastic film. While the respective pairs of wings 7a, 8a of the front and rear waist regions 7, 8 may be formed from the backsheet 3 or laminate of the backsheet 3 and the topsheet 2, it is also possible to use a sheet prepared separately of the topsheet 2 and the backsheet 3 as a stock material of these wings 7a, 8a. Such sheet material is preferably air-permeable and liquid-impervious.

In the sheet strip assembly 22 of the diaper 1, the individual sheet strips 41 may be formed from a hydrophilic or water repellent nonwoven fabric made of thermoplastic synthetic fibers having a basis weight in a range of 10 to 100 g/m$^2$ and a density in a range of 0.05 to 0.1 g/cm$^3$. Alternatively, such nonwoven fabric may be replaced by a soft touch plastic film having a thickness in a range of 0.01 to 0.05 mm. It should be understood here that the density of nonwoven fabric indicated herein is a value measured on the basis of under a load of 3 g/cm$^2$ exerted on nonwoven fabric and a weight of nonwoven fabric per 1 m$^2$. The thermoplastic synthetic fibers forming such nonwoven fabric is preferably crimped synthetic fibers such as crimped composite fibers. The individual sheet strips 41 formed from such fibers can for the tufted sheet strip assembly 22 adapted to be elastically deformable not only in dry condition but also in a wet condition. The sheet strip assembly 22 is easily put in contact with the skin 80 and, in addition, it is unlikely that the sheet strip assembly 22 might unacceptably exert compression on the skin 80 even if the assembly 22 is kept in contact with the skin 80 for a long period. In the case of the individual sheet strips 41 formed from a hydrophilic nonwoven fabric, these individual sheet strips 41 rub the skin 80 contaminated with body fluids such as loose passage so that such body fluids may transfer from the skin 80 onto the individual sheet strips 41 to clean the skin 80. The sheet-like base member 42 constituting the sheet strip assembly 22 may be formed from an elastically stretchable/contractible hydrophilic or water-repellent nonwoven made of thermoplastic synthetic fibers and having a basis weight in a range of 20 to 200 g/m$^2$ or an elastically stretchable/contractible plastic film having a thickness in a range of 0.05 to 0.2 mm. Alternatively, an elastically stretchable/contractible composite sheet obtained by laminating an inelastically stretchable nonwoven fabric or a plastic film with an elastically stretchable/contractible nonwoven fabric or a plastic film. It is also possible to join an elastically stretchable nonwoven fabric or a plastic film to an inextensible nonwoven fabric or a plastic film in the transverse direction X and thereby to obtain a partially elasticized sheet material which may be used as a stock material for the sheet-like base member 42. Furthermore, it is also possible to use an elastically stretchable/contractible sheet material obtained by bonding an elastic member such as a rubber thread in its stretched state to an inextensible nonwoven fabric or a plastic film.

Figure 6:
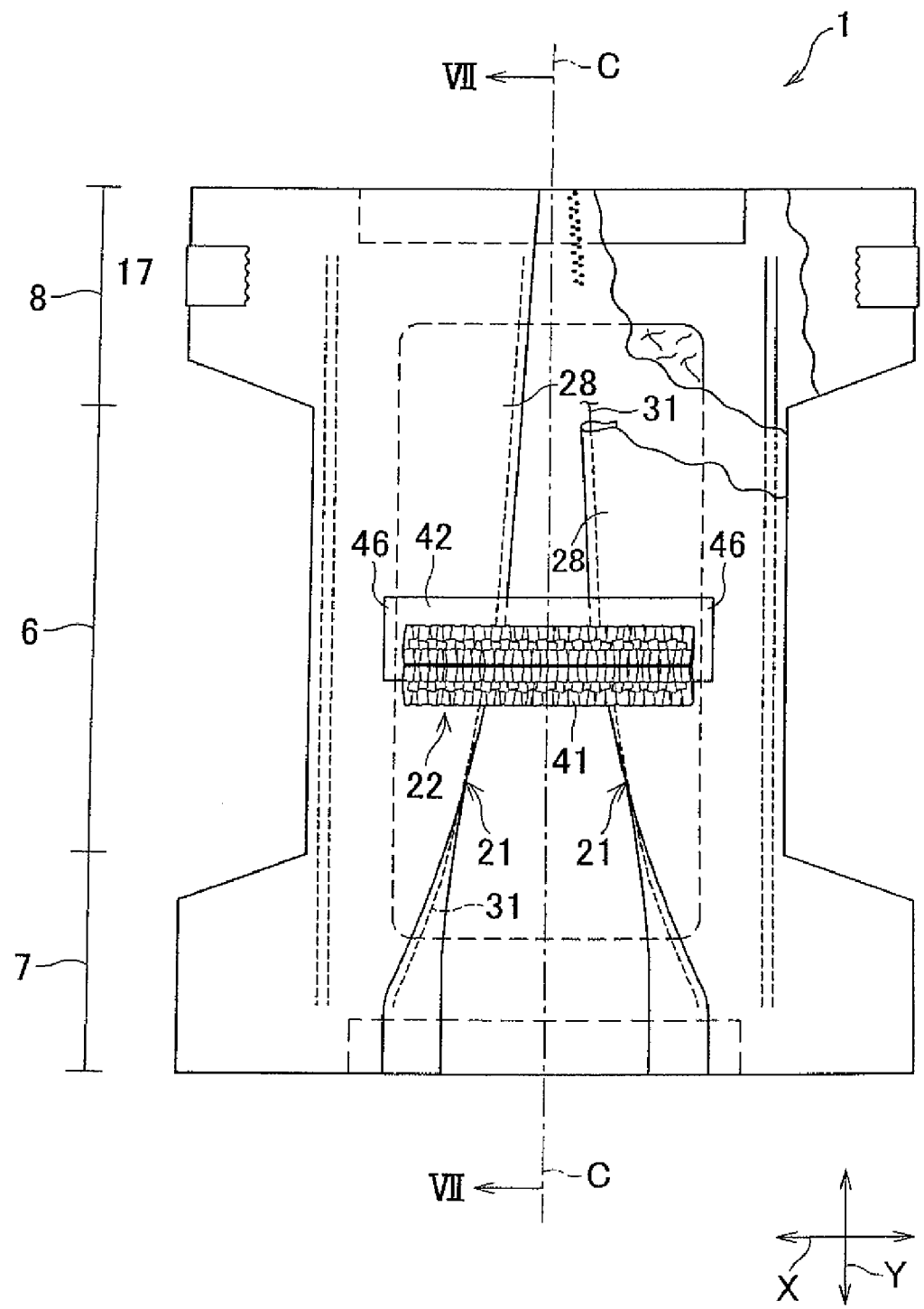
FIG. 6 is a view similar to FIG. 1, showing one preferred embodiment of the present invention.
Figure 7:
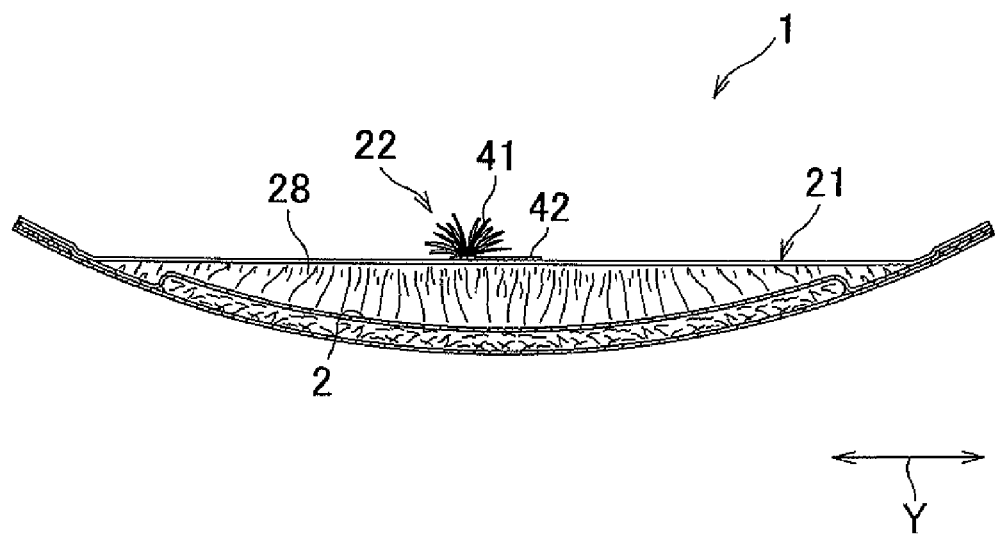
FIG. 7 is a sectional view taken along the line VII-VII in FIG. 6.

FIG. 6 is a view similar to FIG. 1, showing one preferred embodiment of the present invention and FIG. 7 is a sectional view taken along the line VII-VII in FIG. 6 wherein the line VII-VII corresponds to the longitudinal center line C-C. The diaper 1 of FIG. 6 also has a pair of leak-barrier cuffs 21 but each of these leak-barrier cuffs 21 has a width larger than the leak-barrier cuff 21 of FIG. 1. The free edges 28 of the leak-barrier cuffs 21 shown by FIG. 6 obliquely extend and gradually get nearer to the center line C-C and, in the front waist region 7, the leak-barrier cuffs 21 are partially folded outward in the vicinity of the respective free edges 28. A substantial distance between these two leak-barrier cuffs 21 is relatively large in the front waist region 7 and relatively small in the rear waist region 8. The sheet strip assembly 22 extends in the transverse direction X orthogonally to the center line C-C so as to define the innermost side of the diaper 1 and the transversely opposite end zones 46 of the sheet-like base member 42 are bonded to the leak-barrier cuffs 21 from above as viewed in FIG. 7 by a hot melt adhesive (not shown). Unlike the sheet-like base member 42 of FIG. 1, this sheet-like base member 42 is formed from an inextensible nonwoven fabric and consequentially has no elastic stretch ability. However, the sheet strip assembly 22 is spaced from the topsheet 2 and comes in contact with or close to the wearer's skin as the diaper 1 is put on the wearer's body and curves in the back-and-forth direction Y. More specifically, the elastic members 31 associated with the leak-barrier cuffs 21 contract in response to the diaper 1 curving in this manner and, as a result, the free edges 28 of the leak-barrier cuffs 21 are spaced from the topsheet 2. The leak-barrier cuffs 21 spaced from the topsheet 2 in this manner urge the sheet strip assembly 22 to be spaced upward from the topsheet 2. In the diaper 1 according to this embodiment, the free edges 28 of the leak-barrier cuffs 21 serve as elastic biasing means for the sheet strip assembly 22. In this embodiment, the sheet-like base member 42 may be replaced by the sheet-like base member adapted to be stretchable in the transverse direction X as the sheet-like base member 42 of FIG. 1. The sheet strip assembly 22 may be bonded to the sheet strip assembly 21 not in the crotch region 6 but in the front waist region 7 or the rear waist region 8 without departing from the spirit and the scope of the present invention. In such case, the individual hydrophilic sheet strips 41 constituting the sheet strip assembly 22 serve as a sweat-absorbent means adapted to absorb sweat around the wearer's waist.

Figure 8:
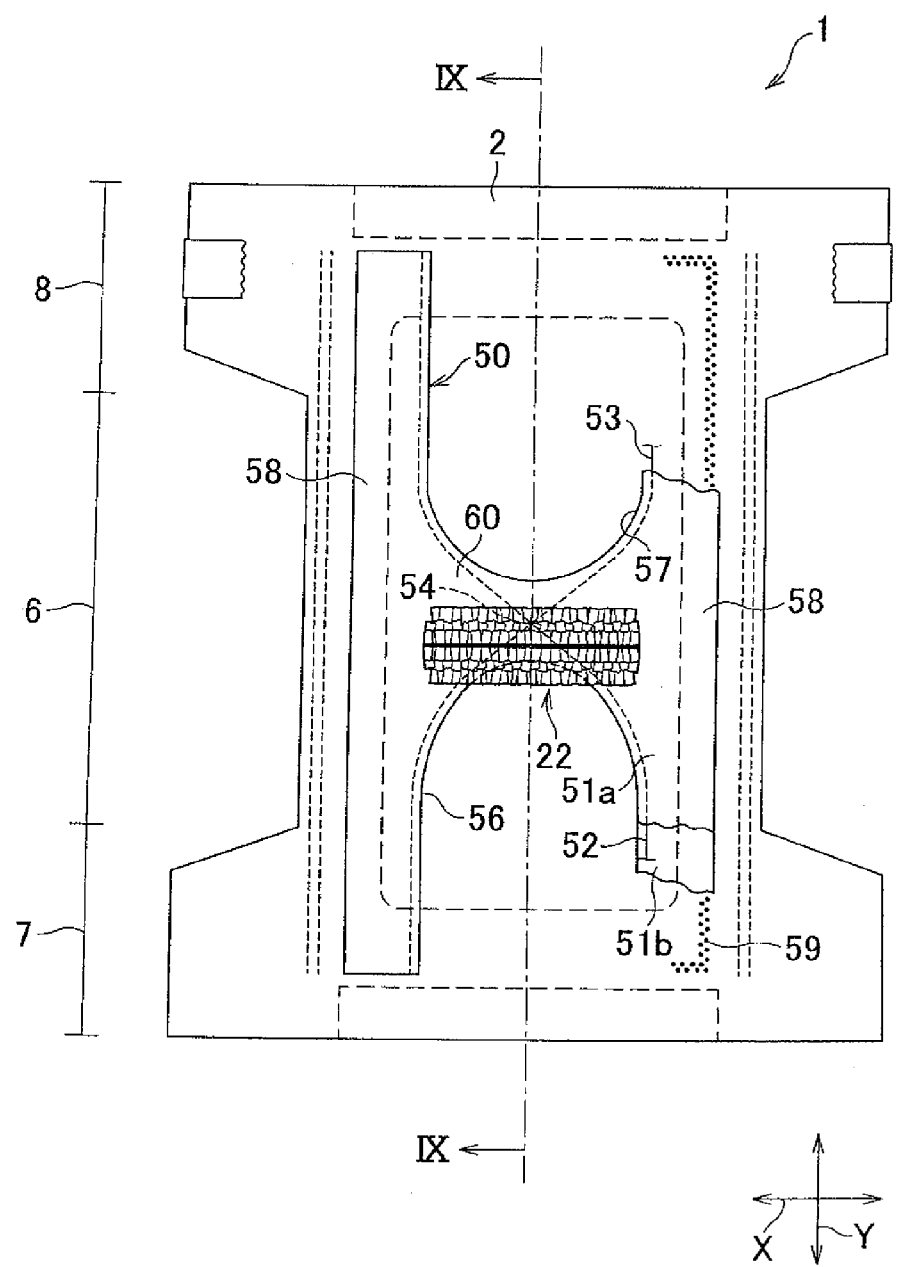
FIG. 8 is a view similar to FIG. 1, showing another preferred embodiment of the present invention.
Figure 9:
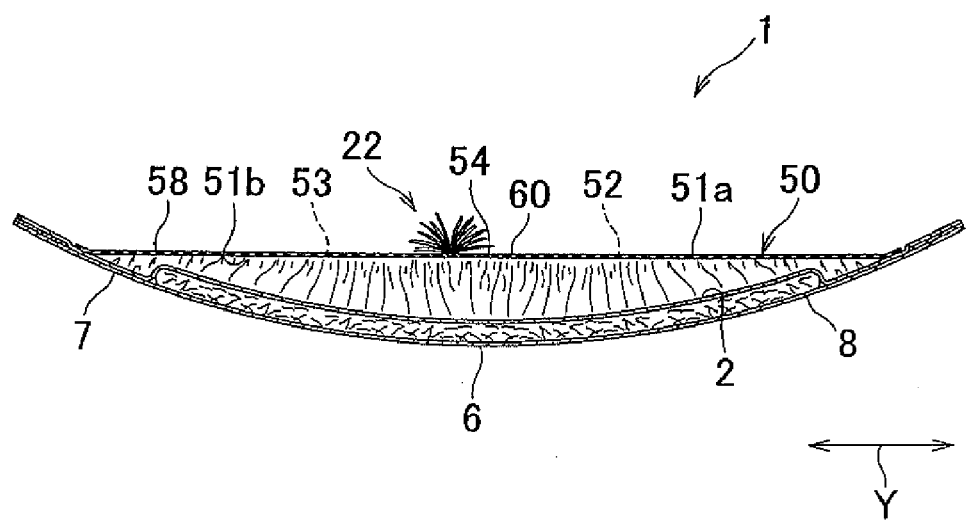
FIG. 9 is a sectional view taken along the line IX-IX in FIG. 8.

FIG. 8 is a view similar to FIG. 1, showing another preferred embodiment of the present invention and FIG. 9 is a sectional view taken along the line IX-IX in FIG. 8. The diaper 1 of FIG. 8 has a substantially H-shaped elasticized sheet 50 provided on the inner side of the topsheet 2. In the elasticized sheet 50, a pair of elastic members 52, 53 extending to intersect to each other and thereby to describe a X-shape are sandwiched in a stretched state between a pair of H-shaped nonwoven fabric layers 51a, 51b which are, in turn, bonded to each other by a hot melt adhesive (not shown) as shown so that these nonwoven fabric layers 51a, 51b may be elastically contractible in the directions in which those elastic members 52, 53 extend. The elasticized sheet 50 is formed with a front notch 56 opening toward the front waist region 7 and a rear notch 57 opening toward the rear waist region 8. Transversely opposite side edges 58 of this elasticized sheet 50 are respectively bonded to the topsheet 2 by a hot melt adhesive 59 and a joint zone 60 joining the side edges 58 to each other is left free from the topsheet 2. The joint zone 60 includes a crossover site 54 of the elastic members 52, 53 and the sheet strip assembly 22 is attached to the nonwoven fabric 51a in the joint zone 60 by means of hot melt adhesive (not shown). The diaper 1 may be put on the wearer's body with the wearer's external genital located within the front notch 56 and the diaper wearer's anus located within the rear notch 57.

As will be apparent from FIG. 9, the elastic members 52, 53 respectively contract between the front waist region 7 and the rear waist region 8 so as to space the elasticized sheet 50 upward from the topsheet 2 in the crotch region 6 as the diaper 1 curves in the back-and-forth direction Y so as to describe U-shape. Thereupon, the sheet strip assembly 22 attached to the elasticized sheet 50 comes in contact with the wearer's skin between the external genital and the anus. It is possible in the diaper 1 of FIG. 8 to attach the leak-barrier cuffs 21 similar to those shown in FIG. 1 to the elasticized sheet 50 along transversely opposite lateral zones thereof, respectively.

Figure 10:
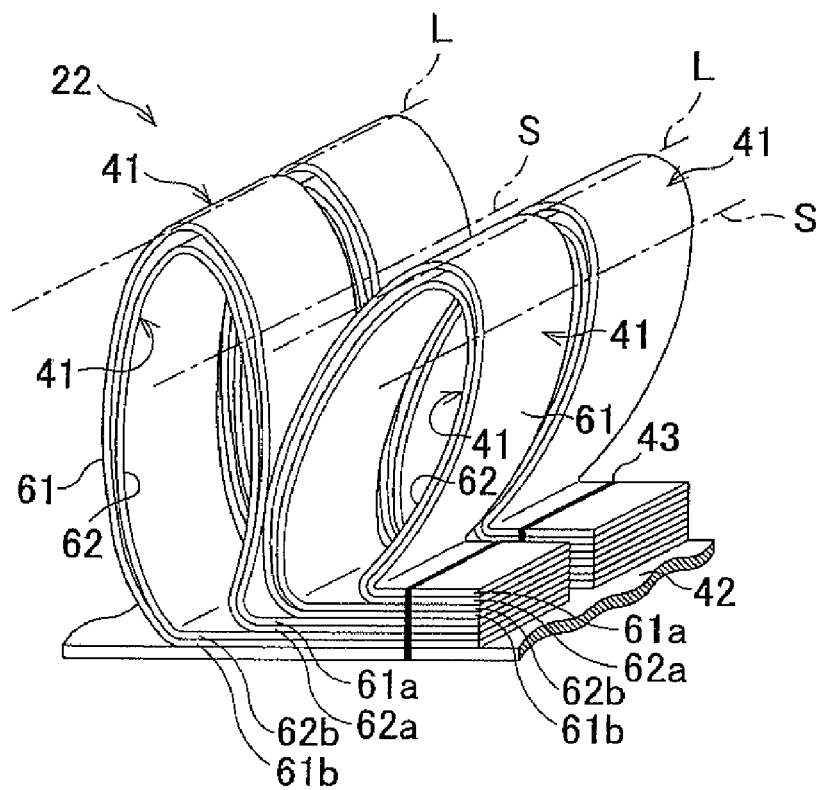
FIG. 10 is a perspective view partially showing an embodiment of a sheet strip assembly.
Figure 11:
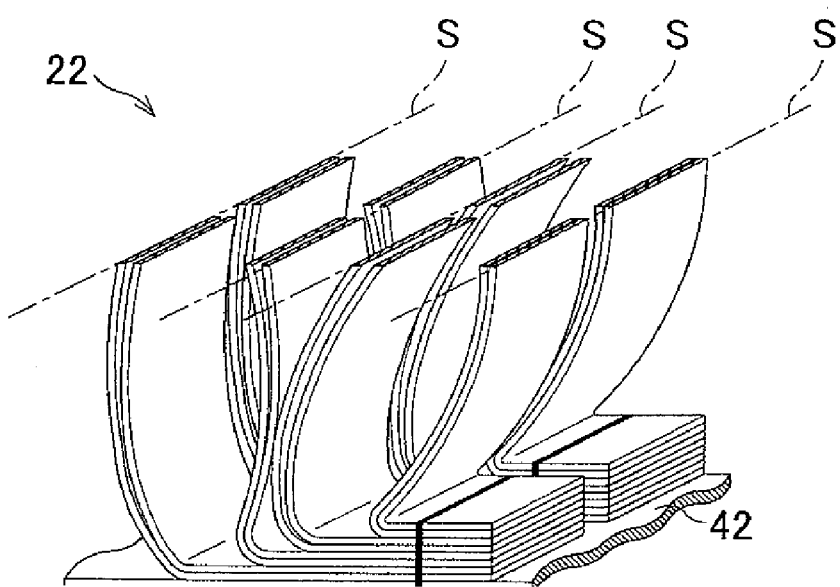
FIG. 11 is a perspective view partially showing another embodiment of the sheet strip assembly.

FIGS. 10 and 11 are perspective view partially showing still other two preferred embodiments of the sheet strip assembly 22 which may be used for the present invention. Each of the sheet strips 41 constituting the sheet strip assembly 22 of FIG. 10 has a double-loop sectional shape and may be obtained, for example, by placing two band-like nonwoven fabric strips 61, 62 upon each other, then folding them along imaginary lines L and heat-sealing or adhesively bonding longitudinally opposite ends 61a, 61b and 62a, 62b of the respective nonwoven fabric strips 61, 62 to the sheet-like base member 42 along the bonding line 43. Compared to the individual sheet strips 41 exemplarily shown in FIGS. 1 through 3, the individual sheet strips 41 of such double-loop type is advantageously characterized in that, even when the individual sheet strip 41 is compressed, for example, by the wearer's body weight from above as viewed in FIG. 10, the sheet strip 41 can easily return to its initial shape as soon as the sheet strip 41 is released from the body weight. Crests of the individual sheet strips 41 of FIG. 10 may be cut off along imaginary lines S in parallel to the sheet-like base member 42 to obtain the sheet strip assembly of FIG. 11, wherein the respective loops defining the individual sheet strips 41 are opened.

Figure 12:
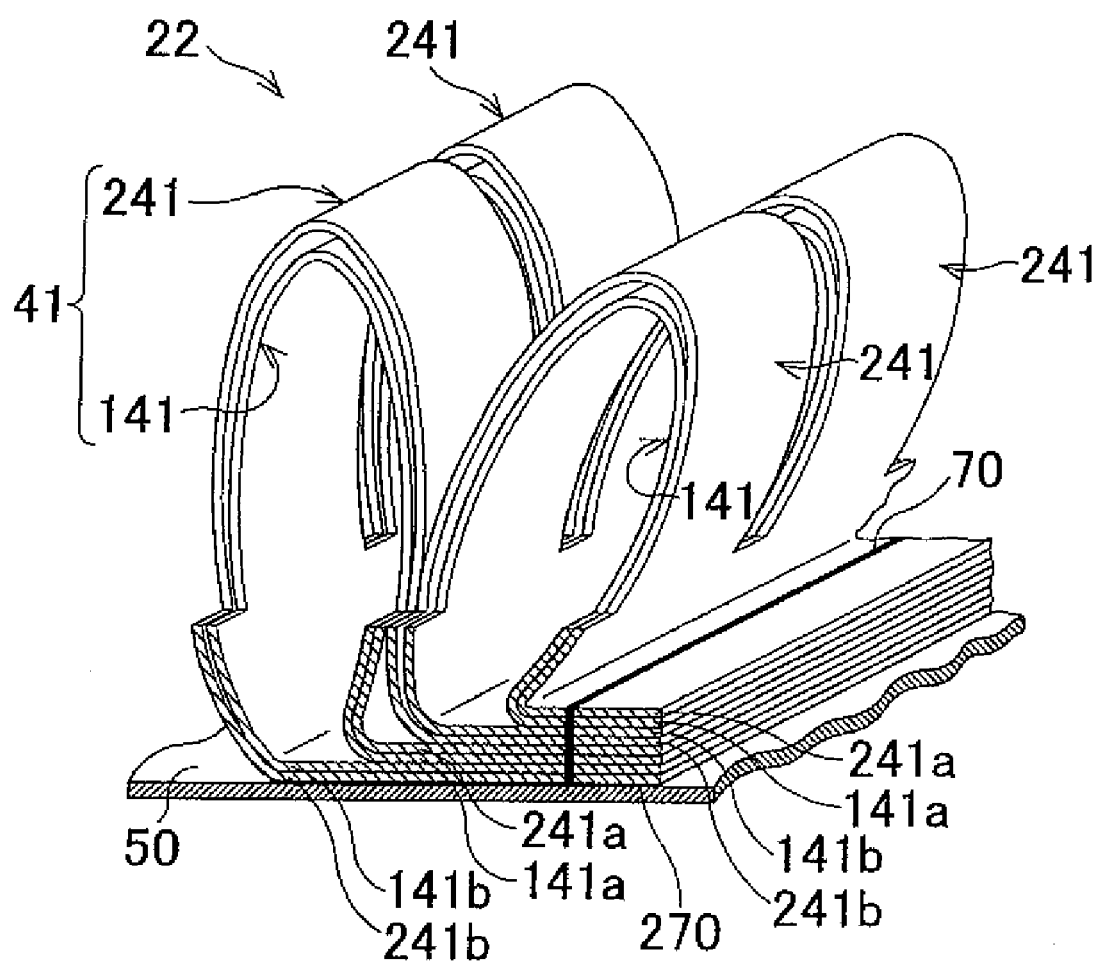
FIG. 12 is a perspective view partially showing still another embodiment of the sheet strip assembly.

FIG. 12 is a view similar to FIG. 10, exemplarily showing still another preferred embodiment of the sheet strip assembly 22. The sheet strip assembly 22 of FIG. 12 also is of a double-loop type comprising a plurality of inner side sheet strips 141 and a plurality of outer side sheet strips 241. The inner side sheet strips 141 have fixed end zones 141a, 141b in common and the outer side sheet strips 241 also have fixed end zones 241a, 241b in common. These fixed end zones 141a, 141b, 241a, 241b are stacked upon one another and bonded together along a welding line 70. The sheet strip assembly 22 constructed in this manner is then bonded to the elasticized sheet 50 shown in FIG. 8 by a hot melt adhesive 270. In this sheet strip assembly 22, the respective common end zones 141a, 141b, 241a, 241b stacked upon one another may function as the sheet-like base member in the place of the sheet-like base member 42 of FIG. 10. In this way, the sheet strip assembly 22 can be directly bonded to the elasticized sheet 50 without use of the sheet-like base member 42 prepared separately of the sheet strip assembly 22.

The present invention makes it possible to manufacture the disposable diaper adapted to prevent urine and/or loose passage from flowing along the wearer's skin.

The entire discloses of Japanese Patent application No. 2006-72959 filed on Mar. 16, 2006 including specification, drawings and abstract are herein incorporated by reference in its entirety.

What is claimed is:
1. A disposable diaper, comprising:
    a crotch region having a longitudinal direction and a transverse direction orthogonal to said longitudinal direction, a front waist region extending forward from said crotch region, and a rear waist region extending rearward from said crotch region, opposite inner and outer surfaces, and a tufted assembly attached to said inner surface in any one of said regions so as to extend in said transverse direction in orthogonal relationship with a center line that extends in said longitudinal direction and bisects widths of respective said regions, said assembly comprising:

a plurality of sheet strips, a base sheet extending in said transverse direction and supporting thereon said sheet strips each having at least one end zone thereof pennanently bonded to said base sheet, and an elastically biasing element adapted to space at least a transversely middle zone of said base sheet from said inner surface in a thickness direction defined from said outer surface toward said inner surface.

2. The diaper defined by claim 1, wherein at least a part of said base sheet is elastically stretchable/contractible in said transverse direction; and end zones of said base sheet opposed to each other in said transverse direction are bonded, in stretched state, to said inner surface so as to ensure that said base sheet serves as said elastically biasing element.

3. The diaper defined by claim 1, further comprising:

on said inner surface of said diaper, a pair of leak-barrier cuffs extending along transversely opposite side edges of said crotch region and further into said front and rear waist regions, each of said leak-barrier cuffs having a fixed edge bonded to said inner surfaced, a free edge extending in parallel to said fixed edges, and an elastic member stretchable in said longitudinal direction and bonded in stretched state to said free edge, wherein said end zones of said base sheet are bonded to respective said free edges so as to ensure that said free edges serve as said elastically biasing element.

4. The diaper defined by claim 1, further comprising:

on said inner surface of said diaper, an elasticized sheet including a first elastic member and a second elastic member extending so as to intersect with each other and to describe an X-shape in said crotch region, wherein said elasticized sheet has lateral zones extending from said crotch region toward said front waist region and said rear waist region, and a joint zone joining the lateral zones to each other, said lateral zones being bonded to said inner surface while said joint zone is left free from said inner surface and includes the intersection of said first elastic member and said second elastic member, said elasticized sheet being elastically stretchable/contractible in directions in which said first elastic member and said second elastic member extend, said assembly being bonded to said joint zone so as to ensure that said elasticized sheet serves as said elastically biasing element.

5. The diaper defined by claim 1, wherein the transversely middle zone of said base sheet is free of direct attachment to the inner surface of said diaper, and is biased by said elastically biasing element, as the elastically biasing element contracts, to be spaced upwardly from the inner surface of said diaper so as to define, between said transversely middle zone of said base sheet and the inner surface of said diaper, a passage for bodily discharge to flow in the longitudinal direction on said inner surface and under the transversely middle zone of said base sheet.

6. The diaper defined by claim 5, wherein at least a part of said base sheet is elastically stretchable/contractible in said transverse direction; and end zones of said base sheet opposed to each other in said transverse direction are bonded, in stretched state, to said inner surface so that said base sheet serves as said elastically biasing element and the transversely middle zone of said base sheet is spaced from the inner surface of said diaper as the base sheet contracts in the transverse direction.

7. The diaper defined by claim 5, further comprising:

on said inner surface of said diaper, a pair of leak-barrier cuffs extending along transversely opposite side edges of said crotch region and further into said front and rear waist regions, each of said leak-barrier cuffs having a fixed edge bonded to said inner surface, a free edge extending along said fixed edge, and an elastic member stretchable in said longitudinal direction and bonded in stretched state to said free edge, wherein said end zones of said base sheet are bonded to respective said free edges so that said free edges serve as said elastically biasing element and the transversely middle zone of said base sheet is spaced from the inner surface of said diaper as the elastic members bonded to the free edges contract in the longitudinal direction.

8. The diaper defined by claim 5, further comprising:

on said inner surface of said diaper, an elasticized sheet including a first elastic member and a second elastic member extending so as to intersect with each other and to describe an X-shape in said crotch region, wherein said elasticized sheet has transversely opposite lateral zones extending in the longitudinal direction from said crotch region toward said front waist region and said rear waist region, and a joint zone joining the lateral zones to each other, said lateral zones being bonded to said inner surface while said joint zone is free of direct attachment to said inner surface and includes the intersection of said first elastic member and said second elastic member, said elasticized sheet being elastically stretchable/contractible in directions in which said first elastic member and said second elastic member extend, said base sheet being bonded to said joint zone so that said elasticized sheet serves as said elastically biasing element and the joint zone and the transversely middle zone of said base sheet is spaced from the inner surface of said diaper as the first and second elastic members contract.

9. A disposable diaper, comprising:

a crotch region having a longitudinal direction and a transverse direction orthogonal to said longitudinal direction, a front waist region extending forward from said crotch region, and a rear waist region extending rearward from said crotch region, opposite inner and outer surfaces, and a tufted assembly attached to said inner surface in any one of said regions so as to extend in said transverse direction, said assembly comprising:

a plurality of sheet strips, a base sheet extending in said transverse direction and supporting thereon said sheet strips each having at least one end zone thereof permanently bonded to said base sheet, said base sheet has a transversely middle zone free of direct attachment to the inner surface of said diaper, and an elastically biasing element biasing the transversely middle zone of said base sheet to be spaced upwardly from the inner surface of said diaper so as to define, between said transversely middle zone of said base sheet and the inner surface of said diaper, a passage for bodily discharge to flow in the longitudinal direction on said inner surface and under the transversely middle zone of said base sheet.

* * * * *